(12) United States Patent
McDevitt

(10) Patent No.: US 6,840,770 B2
(45) Date of Patent: Jan. 11, 2005

(54) EXPANDABLE POLYMER DENTAL IMPLANT AND METHOD OF USE

(76) Inventor: Dennis McDevitt, 9116 Club Hill Dr., Raleigh, NC (US) 27617

( * ) Notice: Subject to any disclaimer, the term of this patent is extended or adjusted under 35 U.S.C. 154(b) by 52 days.

(21) Appl. No.: 10/292,182

(22) Filed: Nov. 12, 2002

(65) Prior Publication Data

US 2003/0124486 A1 Jul. 3, 2003

Related U.S. Application Data

(63) Continuation-in-part of application No. 10/034,344, filed on Dec. 28, 2001.

(51) Int. Cl.[7] .................................................. A61C 8/00
(52) U.S. Cl. ....................................................... 433/173
(58) Field of Search ............................... 433/172, 173, 433/174, 175, 176, 201.1

(56) References Cited

U.S. PATENT DOCUMENTS

| | | | | |
|---|---|---|---|---|
| 4,588,381 A | * | 5/1986 | Caracciolo | 433/173 |
| 4,716,893 A | * | 1/1988 | Fischer et al. | 606/66 |
| 5,268,001 A | * | 12/1993 | Nicholson et al. | 606/72 |
| 5,492,470 A | * | 2/1996 | Anders | 433/169 |
| 6,152,738 A | * | 11/2000 | Aker | 433/173 |
| 6,193,516 B1 | * | 2/2001 | Story | 433/173 |
| 2001/0000486 A1 | | 4/2001 | Story | |

FOREIGN PATENT DOCUMENTS

| | | | | |
|---|---|---|---|---|
| DE | 004321785 C1 | * | 3/1995 | A61C/8/00 |
| DE | 019705571 A1 | * | 9/1998 | A61C/8/00 |
| WO | WO 02/062254 A1 | * | 8/2002 | A61C/8/00 |

* cited by examiner

*Primary Examiner*—Todd E. Manahan
(74) *Attorney, Agent, or Firm*—MacCord Mason PLLC

(57) ABSTRACT

Systems and methods for a dental implant system suitable for an endosteal implant into a jawbone are provided. The systems and methods make use of an tapered, expandable polymer sheath insertable into a jawbone, a tapered implant insertable into the sheath and causing expansion of the sheath upon insertion, and an abutment adapted to be coupled to the implant and permitting the attachment of a dental prosthesis.

31 Claims, 15 Drawing Sheets

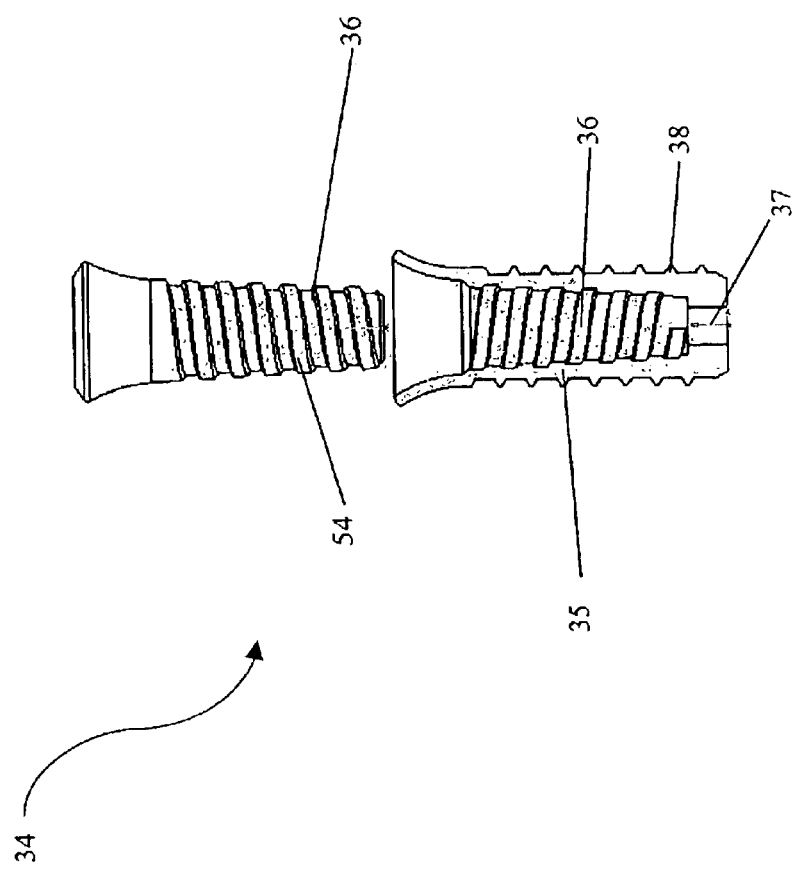

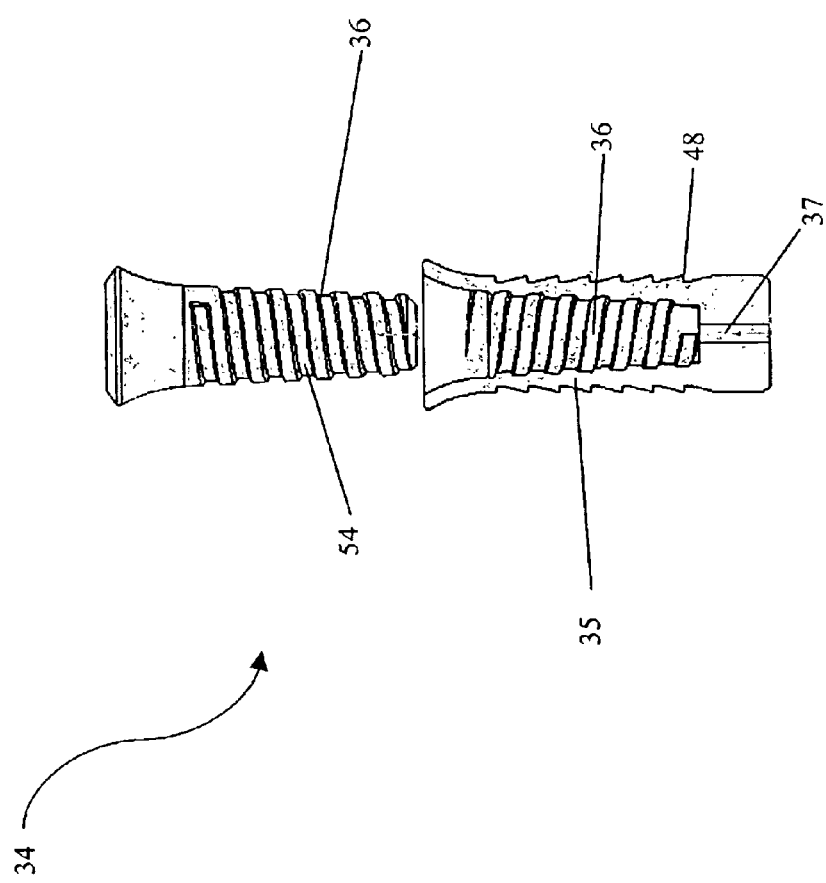

EXPANDABLE POLYMER DENTAL IMPLANT AND METHOD OF USE

CROSS-REFERENCE TO RELATED APPLICATIONS

This nonprovisional utility patent application claims the benefit of one or more prior filed copending nonprovisional applications; a reference to each such prior application is identified as the relationship of the applications and application number (series code/serial number): The present application is a Continuation-In-Part of application Ser. No. 10/034,344 field Dec. 28, 2001, which is incorporated herein by reference in its entirety.

FIELD OF THE INVENTION

This invention generally relates to dental implants and methods for installing such implants.

BACKGROUND OF THE INVENTION

Human teeth vary in shape in accordance with their position and function, but share a common structure. As seen in FIG. 1, a tooth 10 consists of a central pulp 12 that communicates with arteries 14, veins 16, and nerves 18. This pulp 12 is surrounded by a calcareous substance known as dentin 20.

As also seen in FIG. 1, the teeth project from sockets 22, or alveoli dentalis, in the alveolar bone 31 of the maxillae (upper jaw) or mandible (lower jaw).

Each socket 22 is a depression in the bone of the jaw lined by a connective tissue known as the periodontal membrane 24. The portion of the tooth 10 that actually fits into the socket 22 is formed into one or more roots 26. The root 26 is joined to the periodontal membrane 24 and held into the socket 22 by a calcified connective tissue known as the cementum 28. The periodontal membrane 24 serves as a "shock absorber" during the mastication (chewing) process.

The projecting portion of a tooth 10, known as the crown 11, comprises grinding surfaces and is covered by another calcified connective tissue known as enamel 30.

The gums 32, or gingival tissue, cover the base of the crown 11 and project between adjacent surfaces of the teeth 10. Normal, healthy gum tissue 32 serves to anchor teeth in place, as illustrated in FIG. 2.

Gum disease, or periodontal disease, is an inflammation or infection of the gingival tissue. Periodontal disease is caused by a sticky film of bacteria, called plaque. Over time, plaque hardens into calculus (tartar).

Mild inflammation, characterized by red, swollen, and bleeding gums 32, is known as gingivitis. Poor oral hygiene is the primary cause of gingivitis. This early stage of periodontal disease is reversible with proper professional care and good oral home care.

If left untreated, the disease spreads to other supporting structures including alveolar bone 31, producing a more advanced stage of periodontal disease known as periodontitis.

Periodontitis, illustrated in FIG. 3, results in the destruction of alveolar bone 31 and the periodontal membrane 24. This stage is characterized by the gums 32 receding or pulling away from the teeth, resulting in the formation of pockets between the teeth and gums 32.

As the disease progresses, teeth become loose, often necessitating extraction. Thus, periodontal disease is a major cause of tooth loss.

A variety of conditions have been found to contribute the development and advancement of periodontal disease, including tobacco use, genetics, pregnancy, puberty, stress, medications, clenching or grinding of teeth, diabetes, and poor nutrition.

Because of the widespread nature of the disease, there have been a variety of methods devised to implant and secure a dental prosthesis.

The most common type of implant is endosseous, in which a screw or similar device is inserted beneath the jawbone. The device serves to mimic a root structure and protrudes through the gum to hold a prosthesis.

However, when an endosteal implant is not possible due to minimal bone height, a subperiosteal implant can be placed on top of the jaw with the metal framework's posts protruding through the gum to hold the prosthesis.

A conventional prior art endosteal implant system 100, depicted in FIG. 4, typically comprises an implant 110, an inserting device 120, a closure screw 130, and an abutment 140 adapted to receive a dental prosthesis 150.

Conventional implants 110 are cylindrically-shaped members commonly made of rigid, non-expandable biocompatible materials, e.g., a metallic alloy (e.g., titanium alloy) or ceramic (e.g., $Al_2O_3$).

The material can also permit osteo ingrowth (growth of bony tissue), also known as ankylosis, into the implant 110.

The implant 110 may be of a hollow or solid nature. A hollow nature further encourages osteo ingrowth into the implant 110. In either a hollow or solid arrangement, the top portion of the implant 110 protrudes above the gum line and is adapted to receive the closure screw 130 and the abutment 140. The implant 110 may additionally contain holes penetrating the wall of the implant to further promote osteo ingrowth.

The inserting device 120 is a tool adapted to couple the implant 110 and aid in the insertion of the implant 110 within the jawbone 160.

The closure screw 130 is a screw adapted to fit within the top portion of the implant 110. The closure screw 130 serves to cover and protect the top portion of the implant 110 after insertion into the jawbone 160 and prior to attachment of the abutment 140.

The abutment 140 is adapted to fit within the top portion of the implant 110. The abutment 140 serves to permit attachment of a dental prosthesis 150.

In use, the system 110 is employed in a two-part procedure. In the first part of the procedure, the site is prepared for the insertion of the implant 110 by conventional techniques.

As shown in FIG. 5A, the implant 110 is then inserted into a predrilled hole 170 (represented by phantom lines in FIGS. 5A-5D) within the jawbone 160 by using the inserting device 120 to screw (represented by arrow in FIG. 5A) the implant 110 into the jawbone 160 (e.g., with the aid of a ratchet).

The inserted implant 110 is shown in FIG. 5B. Next, as also shown in FIG. 5B, the closure screw 130 is then screwed (represented by arrow in FIG. 5B) into the top portion of the implant 110.

The first part of the procedure is then complete. The second part of the procedure is performed desirably at least several weeks later. This waiting period permits time for osteo (bone) ingrowth into the implant 110. This process however does not reestablish the periodontal membrane/ligament that was destroyed as a result of the tooth loss. The contact between the implant and the bone is a rigid connection with no dampening effect.

After the appropriate waiting period, the second part of the procedure is then performed. First, the closure screw 130 is removed (not shown).

Second, as illustrated in FIG. 5C, the abutment 140 is screwed (represented by arrow in FIG. 5C) into the top portion of the implant 110.

Finally, as shown in FIG. 5D, a conventional dental prosthesis 150 is attached to the abutment 140 using conventional techniques.

As the prior art illustrates, conventional ankylosing implants require the procedure to be at least two-step and require more than one office visit.

Despite their widespread use in prior art for promoting osseointegration, titanium and titanium alloys present certain other challenges to providing an optimal dental implant. Titanium and suitable titanium alloys are orders of magnitude higher in stiffness than human bone, and therefore dental implants formed from such materials transmit most of the forces of mastication. If the implants are cylindrical, the force is predominantly transmitted through the implant to the opposite end, and little or no force is transmitted laterally. Addition of threads can transmit some of the forces of mastication laterally. However, in some cases implants of this design transmit insufficient lateral forces to bone or tissue surrounding the lateral surfaces of the implant and most of the forces are borne by the bone or tissue in-line with the longitudinal or force axis of the implant. This can lead to a phenomenon known as stress shielding of the surrounding bone. Specifically, it has been determined that inadequate stimulation of bone tissue over extended periods causes the bone tissue to be resorbed by the body. This effect becomes apparent when bone surrounding the dental implant is not adequately stimulated due to, for instance, transmission of a majority of forces created during mastication by a stiff dental implant through the implant. The lack of stimulation along of the tissue along the implant can cause saucerization, otherwise known as bone die-back, which progresses around the upper portion of an otherwise healthy dental implant. The loss of bone can lead to destabilization and even loosening of the dental implant. Additionally, once sufficient bone tissue has undergone resorption, portions of the implant body become exposed, and this surface, which is typically textured to provide high surface area, is susceptible to infection.

Therefore, it would be advantageous to design a dental implant able to transmit the forces of mastication to surrounding bone tissue and reduce stress shielding.

Story (U.S. Publication 2001/0000486) describes a dental implant having a force distribution shell to reduce stress shielding. The device according to Story is composed of a metallic core surrounded by a polymeric shell with a modulus of elasticity lower than the metallic core, in order to transfer more of the forces of mastication to surrounding bone tissue. However, Story teaches a cylindrical implant, which may not transfer a sufficient amount of force to prevent stress-shielding. The device as described by Story is a single implant constructed of two materials. This construction does not allow the surgeon to create a significant compression fit that will sustain the initial mastication forces required for immediate loading. The separate component system allows the surgeon to create a very secure compression fit between the implant and surrounding bone tissue that will sustain these immediate load forces.

Thus, there remains a need for a straightforward, cost effective dental implant that can be inserted easily and with a minimal number of procedures or office visits. Further, the need remains for an implant that provides stability, comfort, long-term wear and reduced stress shielding.

SUMMARY OF THE INVENTION

The present invention provides improved dental implant systems and methods of use. The systems and methods according to the present invention utilize an implant system with two discrete components that are tapered and designed for dynamic response and immediate load bearing. The first component is an expandable polymer sheath suitable for placement within a jawbone. The sheath serves as an artificial periodontal membrane. The second component is a rigid implant that is inserted within the polymer sheath and causes expansion of the polymer sheath when fitted within the sheath. An abutment is provided to couple the rigid implant and permits attachment of a dental prosthesis. Both components are tapered to provide for lateral transfer of loading forces onto the surrounding bone. The dental prosthesis is adapted to be used for a single tooth and/or to extend as a bridge over a gap.

The systems and methods also provide for the ability to post-operatively remove the implant in the event that modifications need to be made. By contrast to the present invention, prior art or traditional metallic implant removal is very difficult due to osteo in-growth; once removed the prior art replacement requires another waiting period for proper in-growth to take place as well as healing from the removal.

Other features and advantages of the inventions are set forth in the following specification and attached drawings.

DESCRIPTION OF THE DRAWINGS

FIG. 6B is cut-away view of a dental implant system incorporating features of the invention.

FIG. 6C is a cut-away view of another embodiment of the dental implant system incorporating features of the invention.

The invention may be embodied in several forms as illustrated in the figures and detailed description thereof and as represented in the claims without departing from its spirit or essential characteristics. The scope of the invention is defined by the claims, rather than being limited to the specific description preceding them, although preferred embodiments are set forth. All embodiments properly existing within the meaning and range of equivalency of the claims are therefore intended to be embraced by the claims.

DETAILED DESCRIPTION

Although the disclosure hereof is detailed and exact to enable those skilled in the art to practice the invention, the physical embodiments herein disclosed merely exemplify the invention and for the purposes of illustration and description thereof, and may be embodied in other specific structures.

Dental Implant with Expandable Polymer Sheath

Figure 6A:
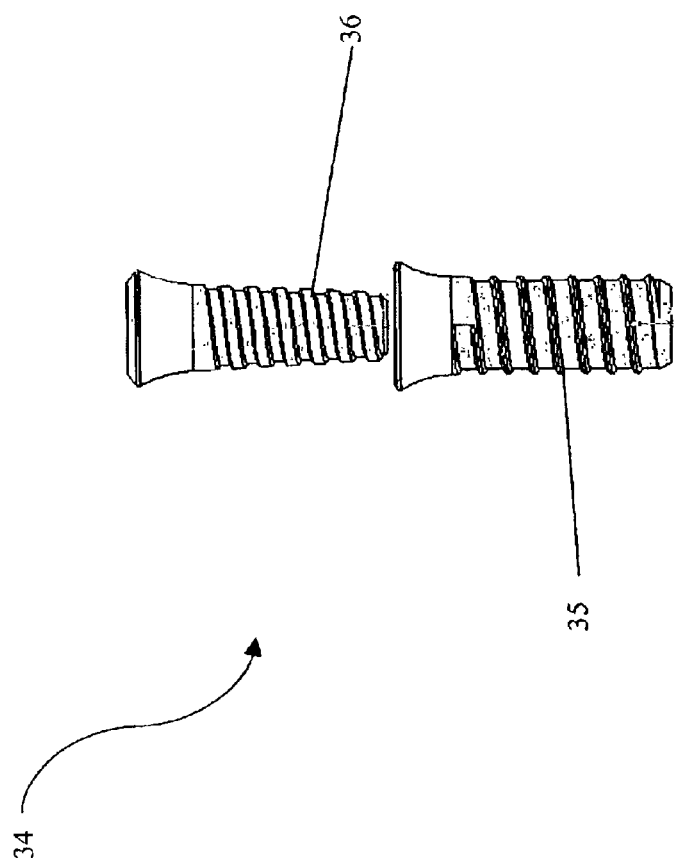
FIG. 6A is a disassembled side view of a dental implant system incorporating features of the invention.
Figure 6D:
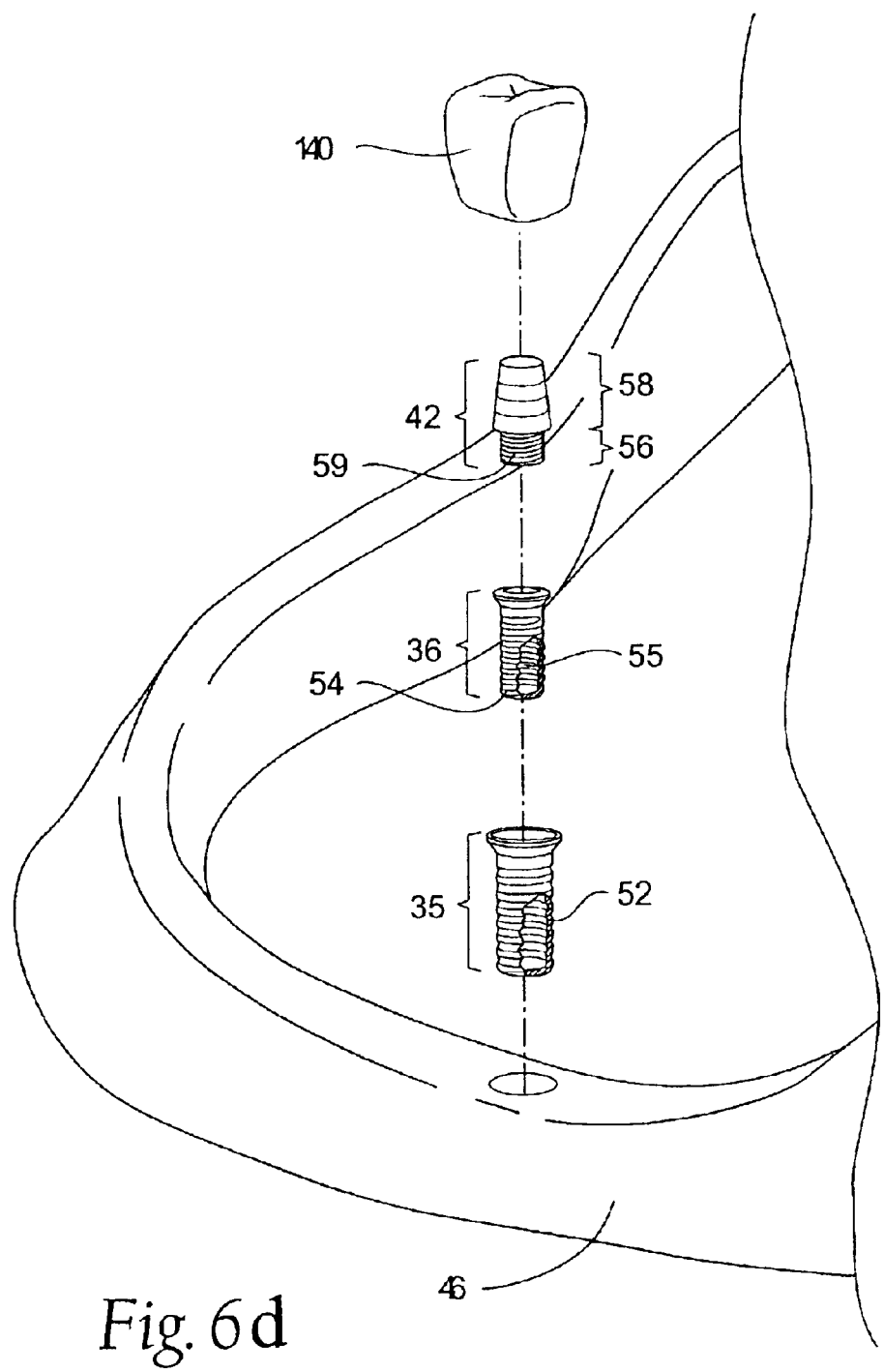
FIG. 6D (prior patent) is a perspective view of a portion of a lower human jawbone, showing, in an exploded view, an alternative dental implant system incorporating features of the invention.

FIG. 6A shows a dental implant system 34 suitable for an endosteal implant into a jawbone. The system comprises a tapered expandable polymer sheath 35, a tapered implant 36, and an abutment 42 permitting the attachment of a dental prosthesis (not shown). These components are designed and constructed to form a system that provides for dynamic response and immediate load bearing of the implant after its installation. Details of each of these system components will now be described in detail.

A. The Expandable Polymer Sheath

As seen in FIG. 6A, the system 34 provides an expandable polymer sheath 35, tapered, more particularly having a Morse taper and/or a taper of approximately 2–3 degrees, where the inside diameter of the sheath decreases from top to bottom, and which is illustrated in FIG. 6A. The sheath 35 is designed, constructed, and configured to receive an implant 36. Importantly, the design of the interior of the sheath is complementary to the exterior of the implant, as shown in FIGS. 6B and 6C. FIGS. 6B and 6C are disassembled views of the system with cut-away views of the polymer sheaths. For example, if the exterior of the implant has threads 54, as shown in FIG. 6B, the interior of the sheath contains complementary threads 52 or grooves to guide the implant down the sheath in a predetermined manner.

The exterior of the sheath may be cylindrical or tapered. It may also have threading 38 to assist in installing and holding the sheath in place. This exterior threading may have the reverse orientation to the interior threading, such that installation of the implant into the sheath does not drive the sheath deeper into the jaw when resistance is met. Alternatively, the sheath may have ribbing, as shown in FIG. 6C, that prevents the sheath from being driven deeper into the jaw during installation of the implant. The sheath also functions as an artificial periodontal membrane, i.e., the sheath 35 mimics the periodontal membrane by performing a like cushioning function.

The sheath 35 is a hollow conical section or tapered body having a closed bottom end portion and an open top end portion. The open top portion is designed, constructed, and configured to receive the implant 36. The bottom end also contains a drive feature 37 that functions to drive or turn the sheath into the bone with the appropriate drive tool during installation. The drive feature can also be used to remove the sheath by unscrewing it from the bone. The drive feature can be shortened, as in FIG. 6B, or elongated, as in FIG. 6C.

The expandable nature of the sheath 35 permits it to receive the implant 36 and ensures a close complementary fitting of the sheath-insert pair. Furthermore, the inner diameter of the sheath 35 is slightly less than the outer diameter of the implant 36, which causes an expansion of the sheath 35 as the implant 36 is inserted into the sheath. This expansion of the sheath upon receiving the complementary implant further serves to secure the sheath 35 and implant 36 combination within the jawbone 46.

Figure 7A:
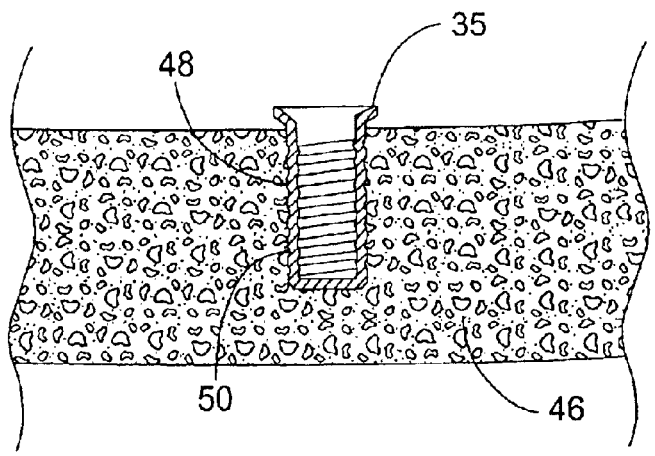
FIGS. 7A-7C are side sectional views of a human jawbone showing the expansion of the polymer sheath component of the system shown in FIG. 6A upon insertion of the implant component into the jawbone.
Figure 7B:
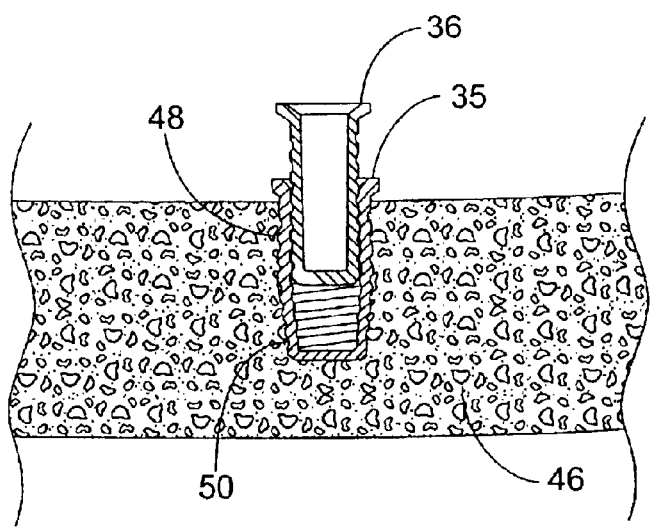
Figure 7C:
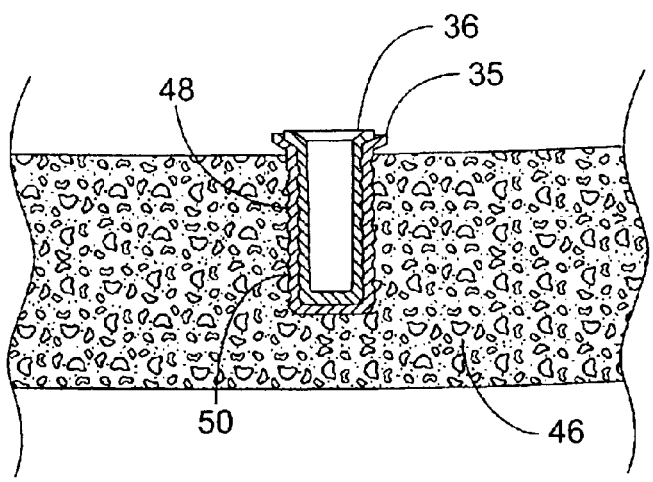

FIGS. 7A-7C detail this expansion process. FIG. 7A illustrates a polymer sheath 35 inserted in a jawbone 46. FIG. 7B shows the expansion of the sheath 35 upon insertion of an implant 36. FIG. 11C shows the implant 36 inserted into the expanded sheath 35.

Suitable materials for the sheath 35 include Ultra High Molecular Weight Polyethylene, High Density Polyethylene (HDPE), Polyurethane Elastomer, and Polypropylene. In general, flexible, biocompatible materials that retain their shape but that can expand and compress under low to moderate pressure can be used to form the sheath according to the present invention.

As also seen in FIGS. 6C, 6D and 7A-7C, the outer surface of the sheath 35 may contain ribs 48. Expansion of the sheath 35 (see FIGS. 7A-7C) compresses surrounding bone structure, further securing and anchoring the sheath 35 within the jawbone 46. The ribs 48 also serve to promote osteo ingrowth, as bony tissue can grow into the grooves 50 between the ribs 48. In a representative embodiment, the ribs 48 are approximately 0.005"–0.020" deep on a sheath 35 that has about a 0.120"–0.200" outside superior diameter with a Morse taper and/or a taper preferably between about 2 to about 3 degrees, more preferably about 2.5 degrees.

The rib 48 design could be straight or threaded and could also be intermittent. The taper and rib design make the sheath and implant combination self-retaining. Additionally, the expansion provided by the implant when inserted into the sheath during installation enhances the self-retaining aspects of the implant system, including the sheath-implant combination. Thus, the expanding, self-retaining taper design of the system permits full use and loading of the implant system immediately after installation for providing complete dental prosthesis installation during as few as one office visit to the dental professional performing the installation procedure.

Thus, the implant system is held into place and supported via multiple levels of fixation, the initial fixation caused by the self-retaining design and expansion of the sheath and the secondary fixation caused by osteo ingrowth.

As the expansion of the sheath 35 and the ribs 48 serve to anchor the sheath 35 within the jawbone 46 at the time of insertion, thereby substantially making it self-retaining, it is not necessary to provide a waiting period after insertion of the implant 36 to permit osteo ingrowth prior to application of additional loading to the sheath-implant combination.

Optionally, the sheath 35 includes holes that penetrate the sheath 35 wall to further permit osteo ingrowth (not shown) to provide additional capacity for osteo ingrowth as a secondary, though substantially less important, means of ensuring the implant's retention after insertion. In the preferred embodiment, however, the sheath 35 does not contain holes, as holes would reduce the total surface area of the artificial periodontal membrane 24 available for load transfer to the surrounding bone and tissue.

Also optionally, as seen in FIG. 6A, the sheath 35 can include internal threads 52 capable of mating with external threads 54 on the outer surface of the implant 36. These threads serve to further secure the implant 36 within the sheath 35.

B. The Implant

As also shown in FIG. 6A, the system also provides an implant 36. The implant 36 is a generally conical section or tapered member insertable into the sheath 35 and causing expansion of the sheath 35 upon insertion of the implant 36. The expansion further secures the sheath 35, as well as the sheath-implant combination, within the jawbone 46, as previously noted.

The implant 36 may be tapered at the top to form an abutment (not shown) such that the top of the implant can receive a prosthetic. Thus, the present invention is able to combine the abutment and implant of prior art systems into a single unit because a removable abutment is no longer needed for the present invention. Prior art required a removable abutment because the prior art systems could not bear normal mastication forces upon initial installment. Only after the supportive tissue had grown around the implant could an abutment and prosthetic be installed. In the intervening period, a closure screw was inserted into the implant to keep the interior of the implant clean and prevent contamination of the surrounding tissue. By contrast, the present invention can bear normal mastication forces upon initial installation and therefore the need for a removable closure screw and abutment, as required by prior art implants, is eliminated by the present invention.

The bottom section of the implant is tapered in order to provide dynamic loading on the surrounding bone and tissue along the entire length of the device surrounded by tissue. The bottom taper is preferably approximately between about 2 to about 3 degrees, more preferably about 2.5 degrees, approximately 0.5 inches/foot. The bottom section of the implant tapers from top to bottom, that is, the diameter of the implant decreases from top to bottom, as shown in FIG. 6A. The implant 36 is designed to insert into the sheath 35. The designs of the exterior of the implant and interior of the sheath are complementary. For example, if the exterior of the implant has threads 54, as shown in FIG. 6A, the interior of the sheath contains complementary threads 52 or grooves to guide the implant down the sheath in a predetermined manner.

The implant 36 is a solid, rigid, and non-expandable member, thereby providing stability and strength to the sheath 35 when inserted into the sheath 35.

Thus the combination of the implant and sheath as described form a tapered dental implant that is self-retaining, provides for immediate full use, and a dynamic response.

In the case where the implant and abutment are two separate elements, the implant 36 is adapted to mate with the abutment 42. In the embodiment illustrated in FIG. 6b, the implant 36 has internal threads 55 that serve to receive the abutment 42.

Figure 1:
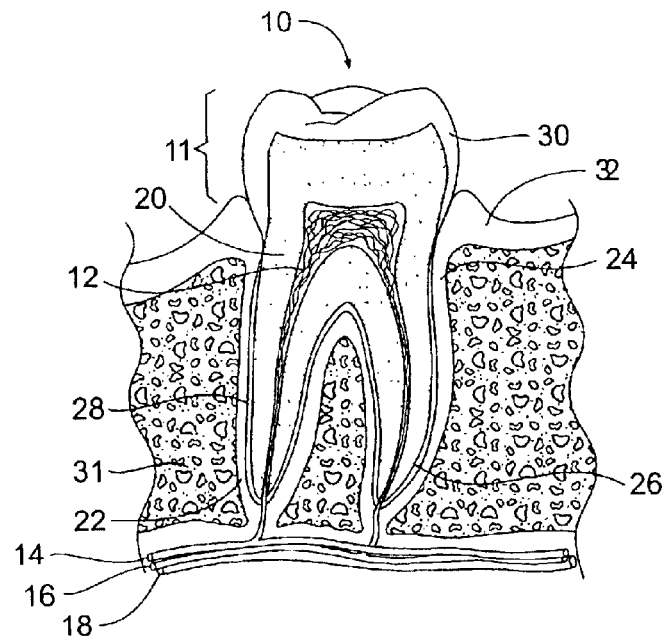
FIG. 1 is a sectional view of a normal human tooth.
Figure 2:
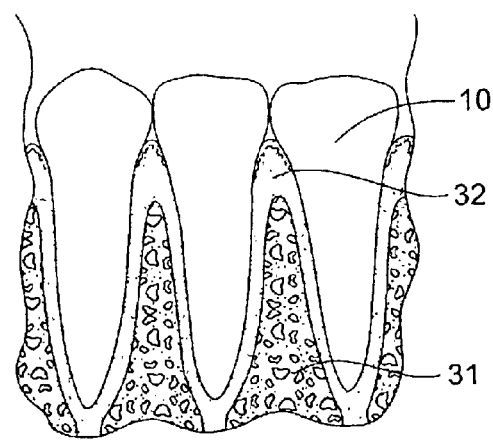
FIG. 2 is a sectional view, with portions removed, of normal, healthy teeth and gums.
Figure 3:
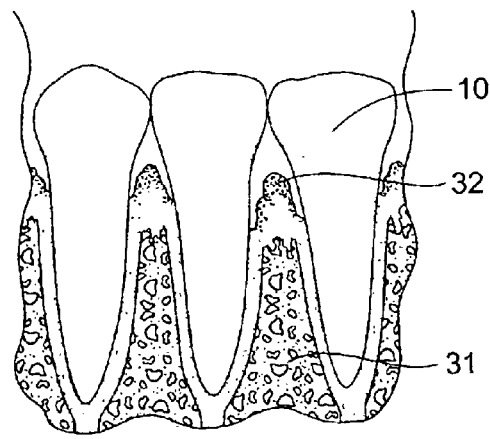
FIG. 3 is a view similar to that shown in FIG. 2 and further illustrating the effects of periodontitis on the teeth and gums.
Figure 4:
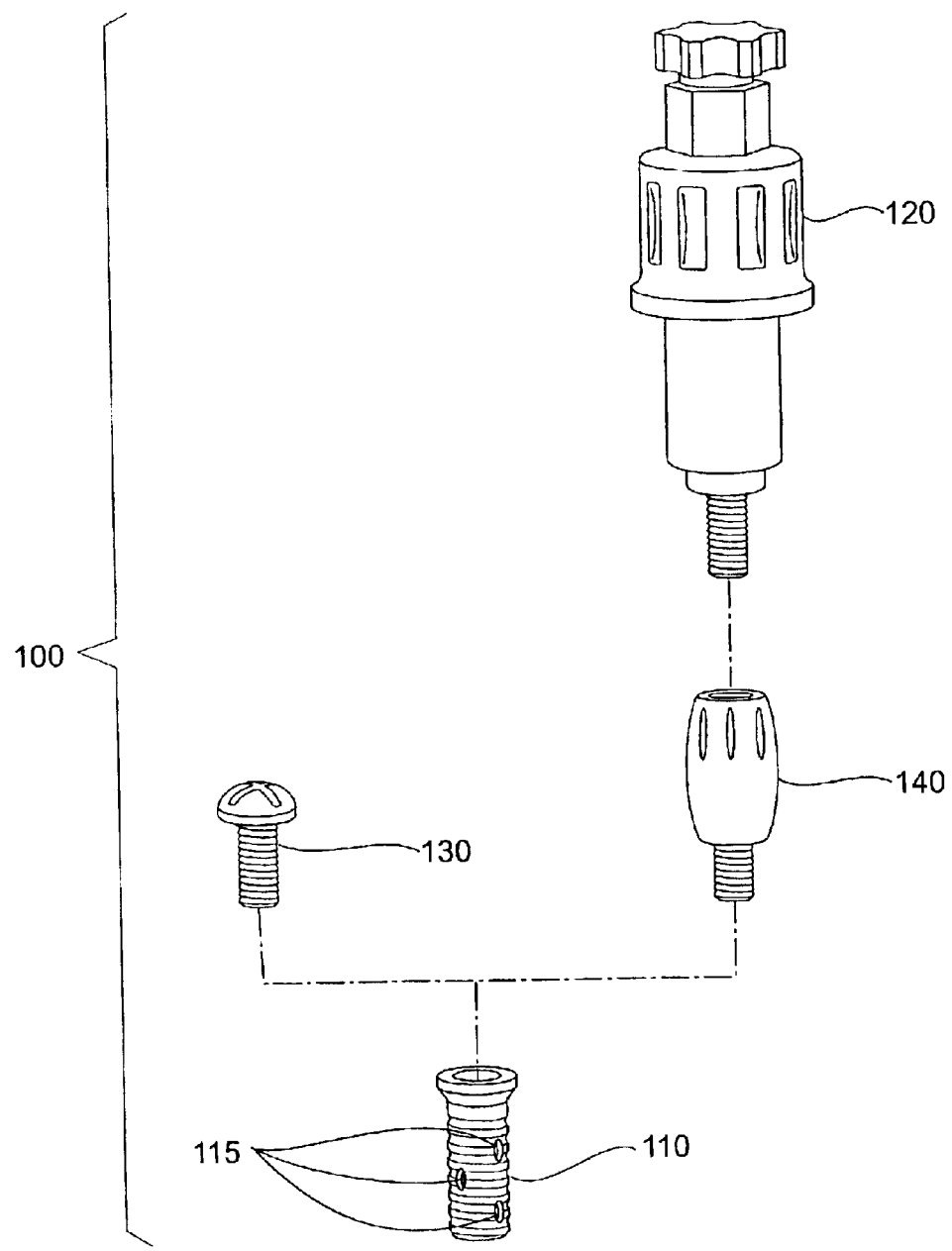
FIG. 4 is an exploded perspective view of a prior art dental implant system.
Figure 5A:
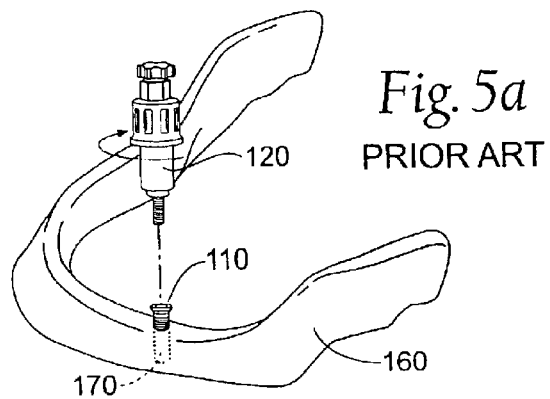
FIGS. 5A-5D are schematic perspective views of a lower human jawbone illustratating the use of the components of the prior art system shown in FIG. 4.
Figure 5B:
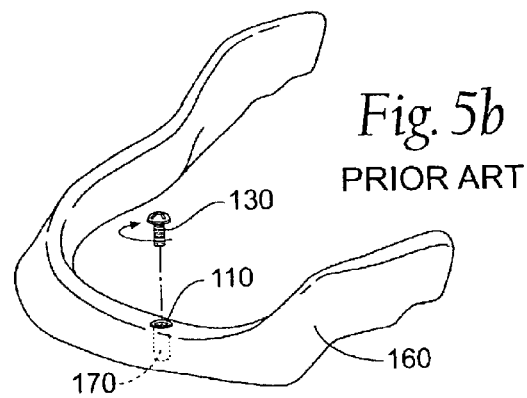
Figure 5C:
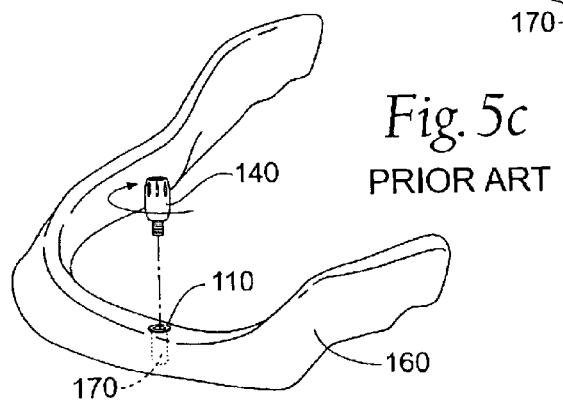
Figure 5D:
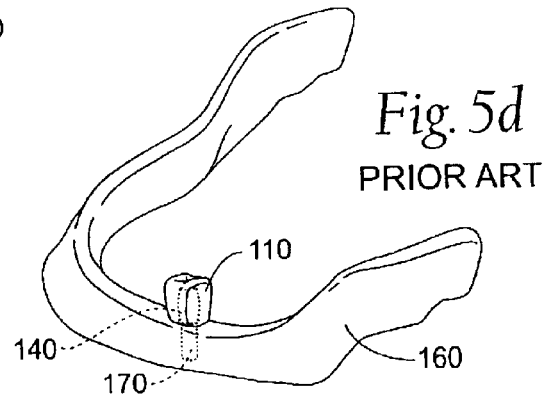

Thus, the implant 36 and sheath 35 serve to mimic the tooth root 26 by providing a load-diffusing, stabilizing structure to which an abutment 42 and/or prosthesis 44, mimicking a tooth crown 11 (see also FIG. 1), are secured within the jawbone 46. Thus, the taper in the implant system thus described diffuses the load along the length of the implant system embedded in the jaw, reducing the stress shielding associated with rigid, cylindrical implants.

The implant 36 can be adapted to be inserted into the sheath 35 in variety of ways. For example, as shown in FIG. 6A, the implant 36 can be provided with external threads 54. In this arrangement, the external threads 54 are adapted to mate with internal threads 52 of the sheath 35. In this arrangement, insertion of the implant 36 is by screwing the implant 36 into the sheath 35.

In the case of a threaded implant, the threading may also incorporate the implant taper into the major thread diameter and/or minor thread diameter, thus including more tapered surface area to increase the lateral transmission of forces.

In an alternate embodiment, the implant 36 does not contain external threads 54. In this arrangement, the implant 36 has an exterior surface that has a Morse taper between 2 to 3 degrees or that is ribbed, or both. In either of these embodiments, unthreaded tapered or ribbed, insertion of the implant 36 is by frictional engagement (i.e., "pressing" of the implant 36 into the sheath 35).

Suitable materials for the implant 36 include inert materials suitable for implantation in the body, e.g., titanium alloy or a stainless steel alloy.

C. The Abutment

As further shown in FIG. 6A, the system also provides an abutment 42. The abutment 42 is either an integral part of the implant, as shown in FIG. 6A, or a separate, solid member adapted to mate with the implant 36. In the case where the abutment is a separate element, as shown in FIG. 6b, the abutment 42 has a first region 56 and a second region 58.

In the embodiment illustrated in FIG. 6b, the first region 56 is cylindrical or tapered and includes external threads adapted to mate with the internal threads 55 of the implant 36. If desired, a conventional dental cement can be additionally applied to further secure the abutment 42 within the implant 36. The second region 58 includes a Morse taper away from the first region 56 and serves to receive the prosthesis 140.

Suitable materials for the abutment 42 include, but are not limited to, titanium or titanium alloys.

In a representative embodiment, the polymer sheath 35 is made of HDPE and is 12 mm×4 mm superior outer diameter with an interior taper preferably between about 2 to about 3 degrees, more preferably about 2.5 degrees. The implant 36 is made of titanium and has a bottom, implantable section 57 that has an 11 mm×3.5 mm superior outer diameter with a taper preferably between about 2 to about 3 degrees, more preferably about 2.5 degrees, and an incorporated abutment 42. The incorporated abutment is also preferably made of titanium and has an 5 mm×3 mm inferior outer diameter with a taper of between about 2 to about 3, preferably, about 2.5 degrees.

II. Use of Implant

The system 34 can be employed in the replacement of either a single tooth or of multiple teeth, as will now be described. While periodontal disease is a primary cause of tooth loss, it should be understood that the system 34 is suitable to treat tooth loss resulting from other causes.

A. Use in Replacement of Single Tooth

In using the system 34 in the replacement of a single tooth, the site is first prepared by conventional techniques. Preparation of the site may involve drilling a hole that is the approximate width of the unexpanded sheath such that an interference fit of the dental implant system into the tissue can be obtained. Alternatively, the site may be prepared by tapping a hole of the proper size and thread dimensions such that a threaded sheath can threaded into the hole and retained by the surrounding tissue.

Figure 8:
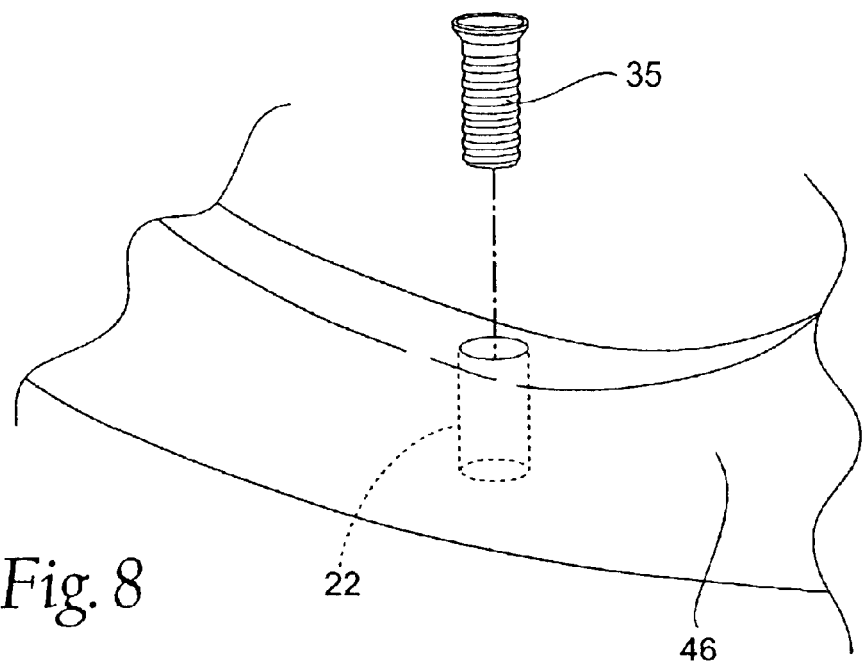
FIG. 8 is a side perspective view of a portion of a lower human jawbone showing the insertion of the polymer sheath component of the system shown in FIG. 6A into the jawbone.

Next, as seen in FIG. 8, the polymer sheath 35 is inserted (depicted by dot-dash line in FIG. 8) into the prepared site using an insertion device, e.g., by use of a mandrel or screwdriver. The insertion device is tapered to hold the sheath in place for secure insertion to the proper height. The sheath is inserted first and separate from the implant.

Figure 9:
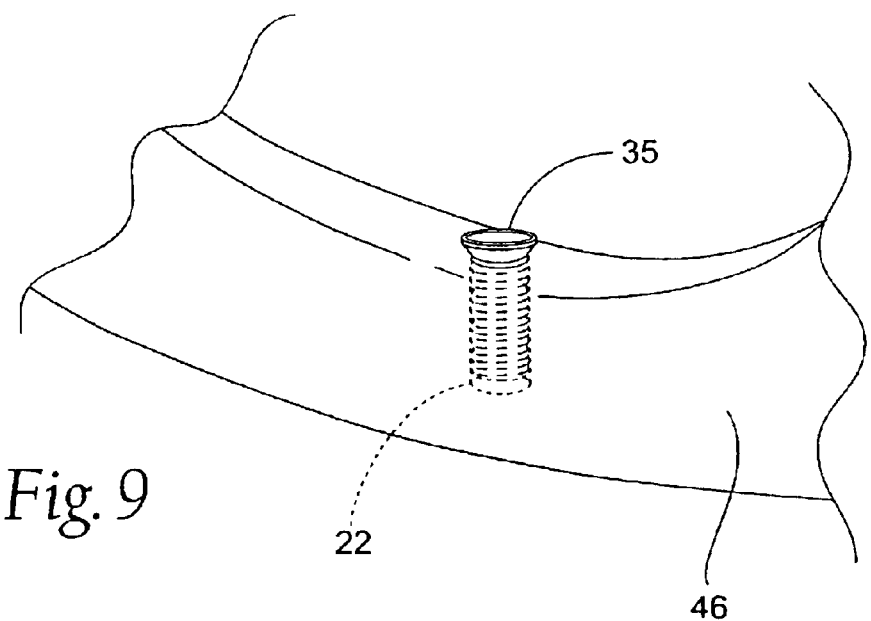
FIG. 9 is a view similar to FIG. 8 showing the polymer sheath inserted into the jawbone.

FIG. 9 illustrates a polymer sheath 35 after insertion into a jawbone 46.

Figure 10:
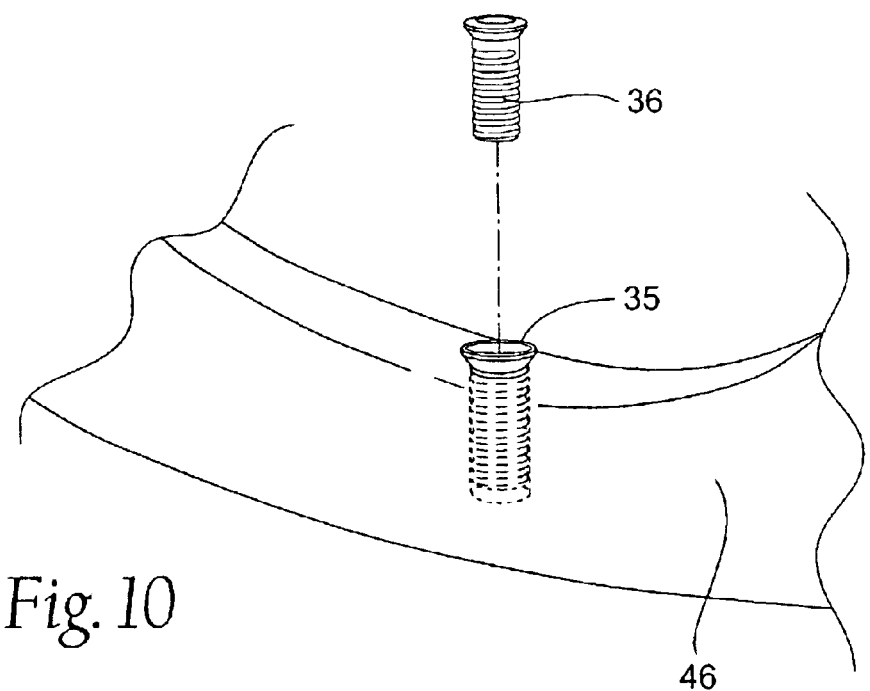
FIG. 10 is a view similar to FIG. 9 showing the insertion of the implant component of the system shown in FIG. 6 into the polymer sheath.

Then, as shown in FIG. 10, the implant 36 is inserted (depicted by dot-dash line in FIG. 10). As previously noted, the implant 36 can include external threads 54 or ribs (not shown). If the sheath and implant have external threading, these threadings may have the reverse orientation, such that installation of the implant into the sheath does not drive the sheath deeper into the jaw when resistance is met.

If the implant 36 includes external threads 54, the implant 36 is screwed into the sheath 35 with the use of a tool, e.g., a screwdriver.

If the implant 36 includes a simple tapered or ribbed taper, the implant 36 is inserted by frictional engagement, e.g., pressing with the aid of a mandrel. The implant 36 is thereby compressed into the sheath 35, which secures it in the sheath 35 and to the bone 46 via the compression forces exerted from the elastic polymer sheath 35. Installation of the implant initially has little resistance; however, the resistance will increase as the implant progresses into the sheath because as the implant progresses into the sheath the outside diameter of the implant and the inside diameter of the sheath will contact and progressively exert increasing resistance against one another. Because the sheath is made of flexible material, the insertion of the implant into the sheath will cause the sheath to expand into the surrounding tissue. The resistance met while inserting the implant in to the sheath is due to the resistance of the sheath and of the tissue surrounding the sheath. Thus, proper support of the implant will be provided by the compression of the sheath between the surrounding tissue and the metallic implant when it is advanced to the proper depth within the sheath.

Figure 11:
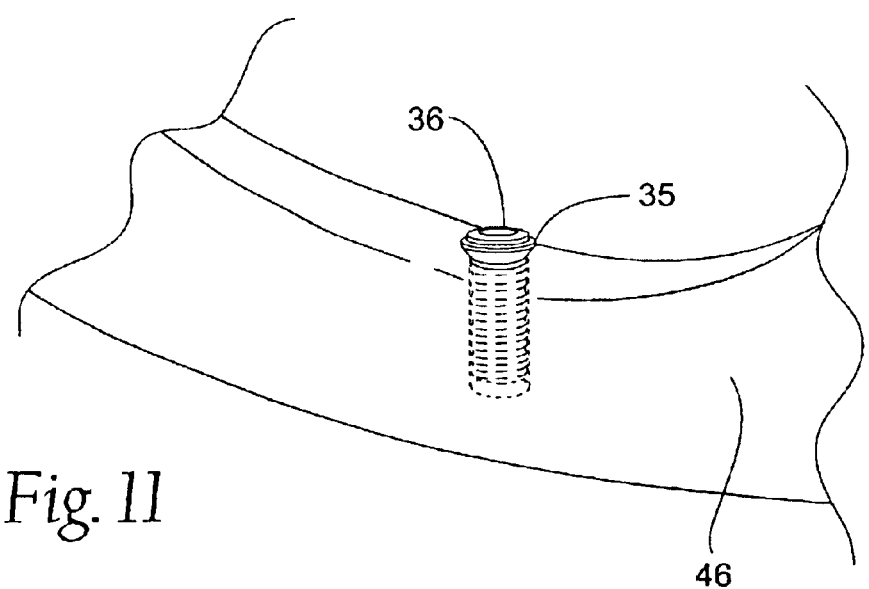
FIG. 11 is a view similar to FIG. 10 showing the implant inserted into the polymer sheath.

FIG. 11 illustrates an implant 36 after insertion into a sheath 35 within a jawbone 46.

Figure 12:
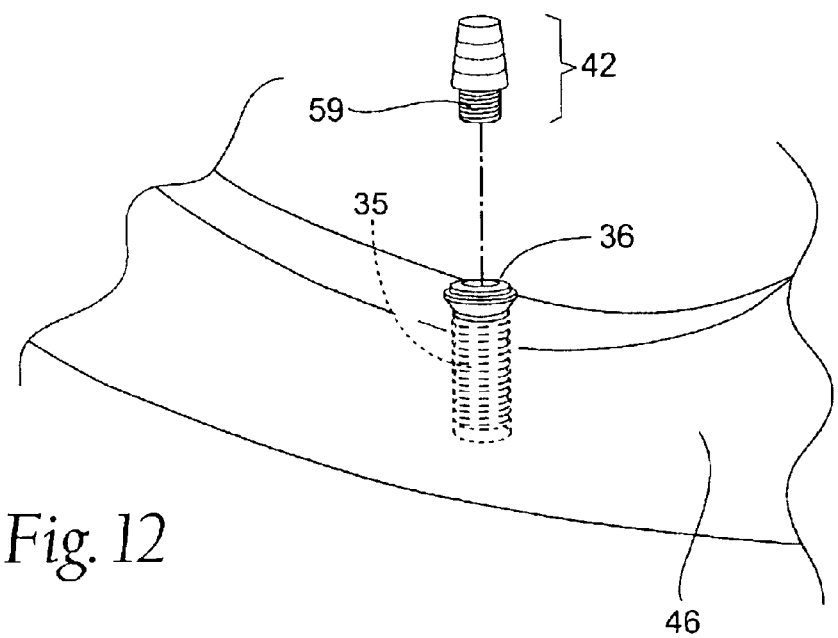
FIG. 12 is a view similar to FIG. 11 showing the coupling of the abutment component of the system shown in FIG. 6 with the implant.

Next, as shown in FIG. 12, the abutment 42 is inserted (depicted by dot-dash line in FIG. 12) into the implant 36, e.g., by screwing the threaded first region 56 into the threaded top end portion of the implant 36.

Figure 13:
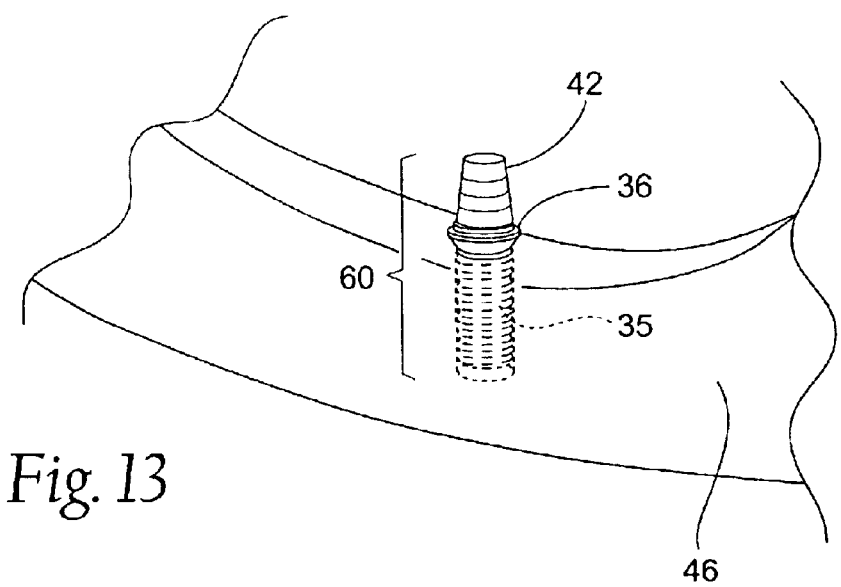
FIG. 13 is a view similar to FIG. 12 showing the abutment component coupled to the implant.

FIG. 13 illustrates an abutment 42, implant 36, and sheath 35 after insertion into a jawbone 46. Together, the abutment 42, implant 36, and sheath 35 form a support structure 60 for securing a dental prosthesis 44.

Alternatively, if the abutment is incorporated integrally into the implant, as shown in FIG. 6A, installation can proceed immediately to attaching the dental prosthesis to the abutment.

Figure 14:
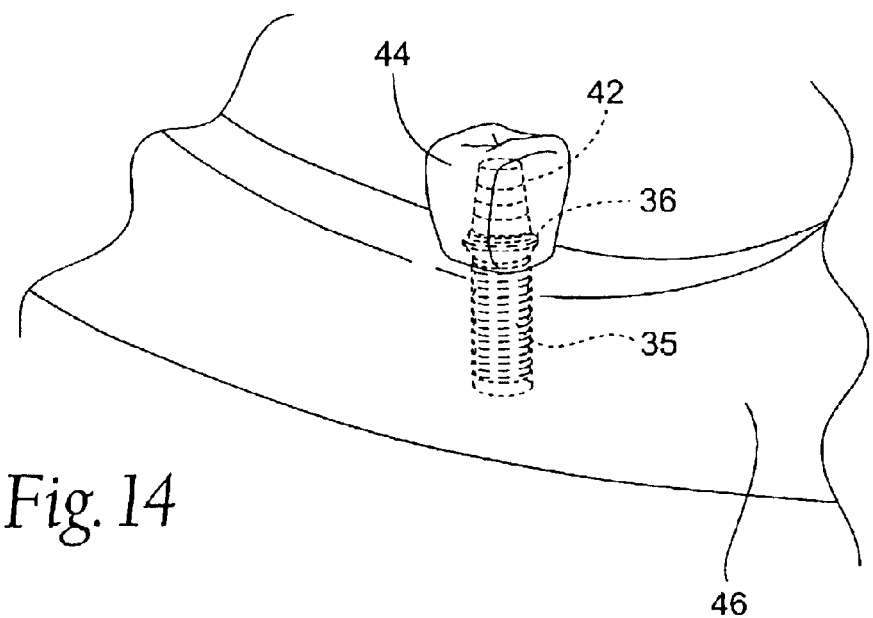
FIG. 14 is a view similar to FIG. 13 showing a dental prosthesis attached to the abutment.

Finally, as FIG. 14 shows, a dental prosthesis 44 is attached to the abutment 42 using conventional techniques.

As no waiting period is needed to allow for osteo ingrowth, the system 34 provides for the insertion of the sheath 35, implant 36, and abutment 42 and the attachment of a prosthesis 44 all within a single office visit. This results in both time and cost savings.

In some cases, it may be desirable to carry out the described procedure over multiple office visits to allow the gum and soft tissue time to heal prior to installing the prosthesis 44. In this case, the sheath 35 and implant 36 can be inserted in the first office visit. A cover screw is then inserted into the implant 36 to cover and protect the implant 36 between office visits (not shown). The abutment 42 can then be inserted and prosthesis 44 attached during a subsequent visit or visits.

B. Use of System in Replacement of Multiple Teeth

While use of the system 34 has been described in relation to the replacement of a single tooth, it is often necessary to replace multiple teeth or an entire set of teeth.

Use of the system 34 when a person is missing multiple teeth (partially edentulous) will now be described.

Figure 15A:
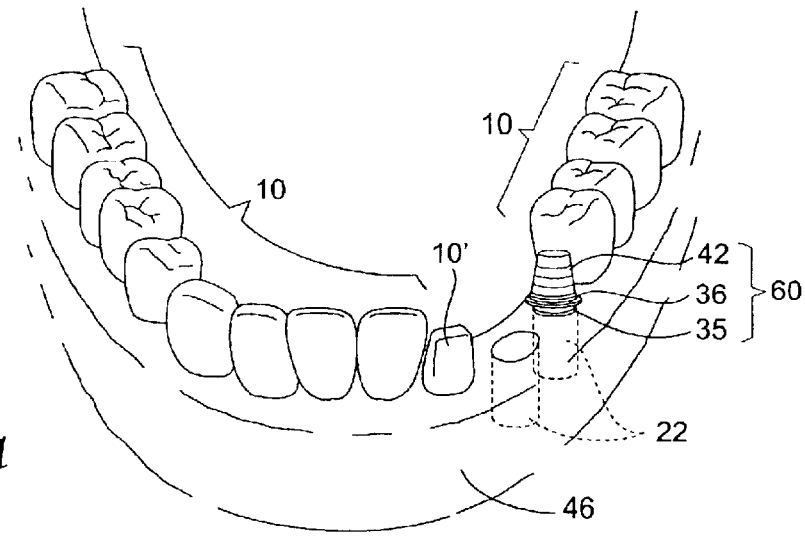
FIGS. 15A and 15B are front perspective views of a lower human jaw bone having a gap of missing teeth and further showing the use of the system shown FIG. 6A in a procedure for the insertion of a dental bridge to fill the gap.
Figure 15B:
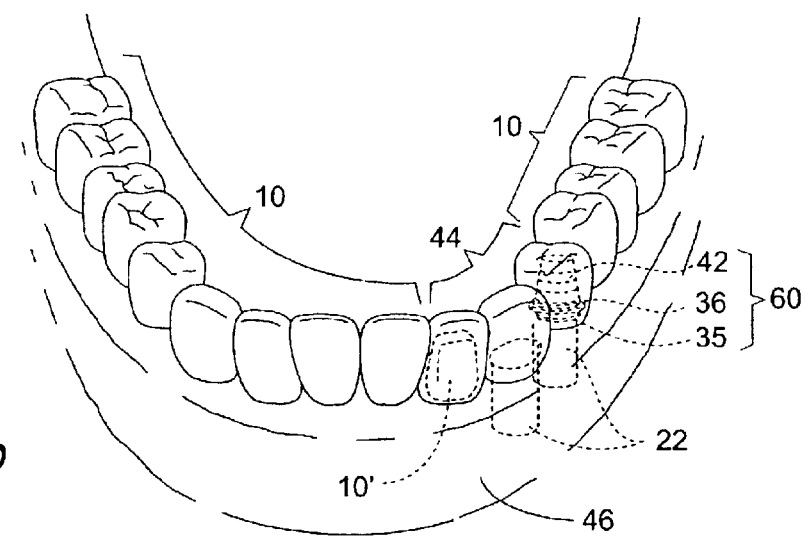

FIGS. 15A and 15B illustrate the use of the system 34 with bridgework (see also FIG. 6A). Multiple teeth are commonly replaced using bridgework. For example, a prosthesis 44 covering a gap caused by multiple missing teeth can be anchored at one end by an abutment 42 and at another end by adhesion to a prepared natural tooth 10'. Typically, the prepared natural tooth 10' is prepared by removal of a portion of enamel 30 and dentin 20 (see also FIG. 1). The prosthesis 44, anchored at both ends, serves as a "bridge" over the gap.

As FIG. 15A shows, a support structure 60 is inserted into the socket 22 of a missing tooth (depicted by phantom lines in FIGS. 14A and 14B) at one end of the gap, as previously described.

As FIG. 15B illustrates, a prosthesis 44 is adhesively attached, using conventional techniques, at one end to the abutment 42 and at the other end to a prepared natural tooth 10' at the opposite end of the gap. Thus, the prosthesis 44 extends over the gap to form a bridge.

Figure 16A:
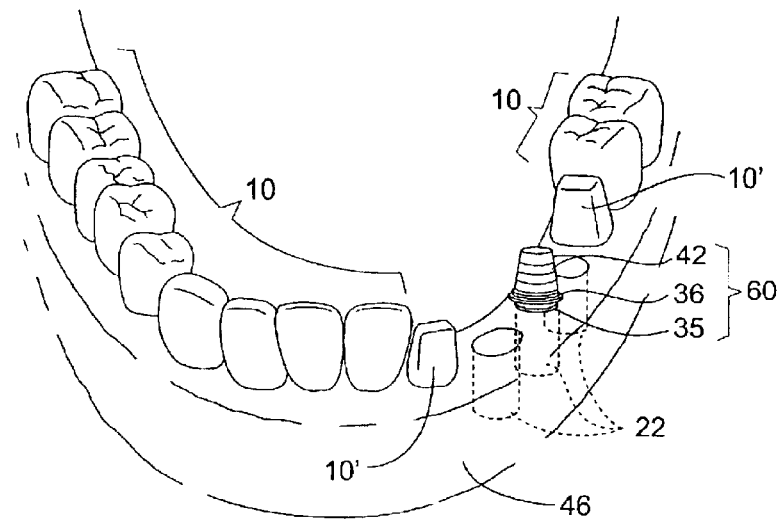
FIGS. 16A and 16B are front perspective views of a lower human jaw bone having a gap of missing teeth and further showing the use of the system shown FIG. 6A in an alternative procedure for the insertion of a dental bridge.
Figure 16B:
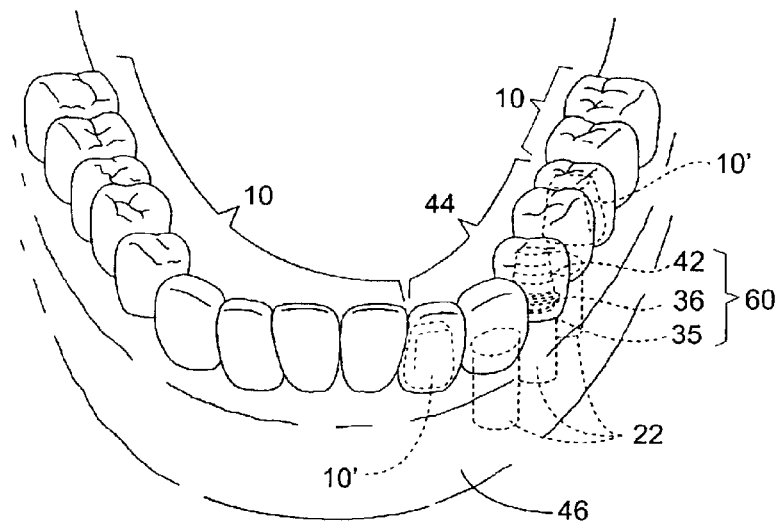

Alternately, as illustrated in FIGS. 16A and 16B, the system 34 can be employed to cover an extended gap. As FIG. 16A shows, the support structure 60 is placed in the socket 22 of missing tooth (depicted by phantom lines in FIGS. 16A and 16B) in the center of a large gap.

As seen in FIG. 16B, the prosthesis 44 is anchored in the center by the abutment 42 and attached at each end to a prepared natural tooth 10' by conventional techniques.

Figure 17A:
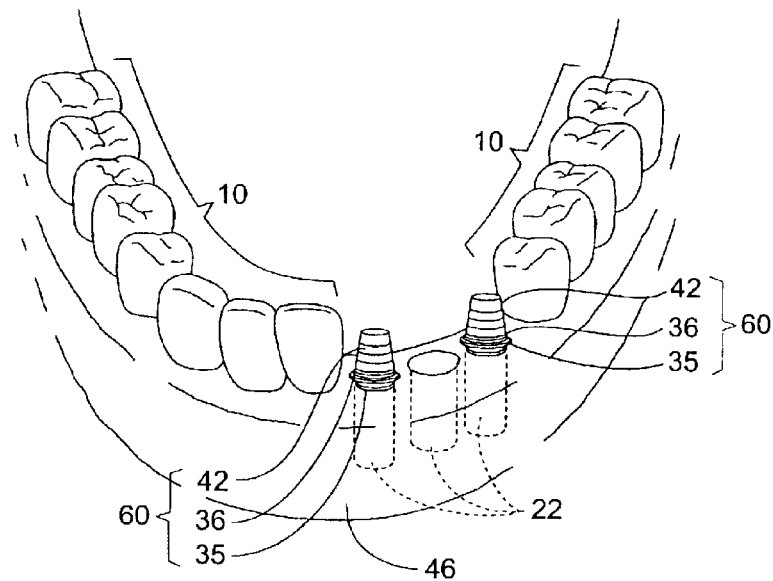
FIGS. 17A and 17B are front perspective views of a lower human jaw bone having a gap of missing teeth and further showing the use of the system shown FIG. 6A in an another alternative procedure for the insertion of a dental bridge.
Figure 17B:
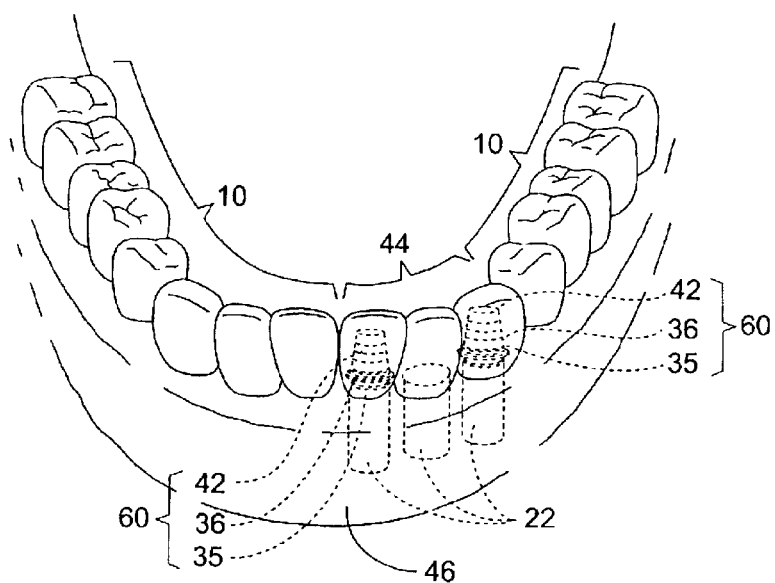

In an alternate arrangement, illustrated in FIGS. 17A and 17B, multiple support structures 60 can be employed to assist in covering a large gap.

As FIG. 17A shows, two support structures 60 are placed in the sockets 22 of missing teeth (depicted by phantom lines in FIGS. 17A and 17B) at opposite ends of a large gap.

As seen in FIG. 17B, the prosthesis 44 is anchored at each end by an abutment 42, as previously described.

The above illustrations of use of the system 34 with bridgework are merely illustrative. It is to be understood that the system 34 can be employed in a variety of other bridgework techniques.

The above described embodiments of this invention are merely descriptive of its principles and are not to be limited. The scope of this invention instead shall be determined from the scope of the following claims, including their equivalents. Certain modifications and improvements will occur to those skilled in the art upon a reading of the foregoing description. All modifications and improvements have been deleted herein for the sake of conciseness and readability but are properly within the scope of the following claims.

What is claimed is:

1. A dental implant system comprising:

a tapered, expandable, biocomparible polymer sheath suitable for placement within a jawbone; and a rigid implant fitting within the polymer sheath and causing expansion of the polymer sheath when fitted within the sheath, the expansion providing for immediate use and loading of the implant, the rigid implant having a tapered bottom inculding a gradual taper along a substantial length of the implant for insertion into the sheath; the taper designed and constructed to diffuse forces along the length of the implant surrounded by tissue to reduce stress-shielding;

thereby providing a self-retaining system to provide a support structure for a dental prosthesis.

2. The system as in claim 1, wherein the polymer is selected from the group consisting of Ultra High Molecular, Weight Polyethylene, Polypropylene, High Density, Polyethylene, and Polyurethane Elastomers.

3. The system as in claim 1, wherein the implant system provides multi-level fixation of the implant-sheath combination.

4. The system as in claim 1, wherein the tapers of the sheath and implant range from about 2 to about 3 degrees.

5. The system as in claim 1, wherein the tapers of the sheath and implant are about 2.5 degrees.

6. The system as in claim 1, wherein in the implant is made of titanium or an alloy thereof.

7. A system as in claim 1, wherein the implant is made of stainless steel or an alloy thereof.

8. A system as in claim 1, wherein the polymer sheath has an exterior surface that is threaded.

9. A system as in claim 1, wherein the polymer sheath has an exterior surface that is ribbed.

10. A system as in claim 1, wherein the polymer sheath has an interior surface that is threaded, and wherein the implant has an exterior surface that is threaded, and whereby the interior surface of the polymer sheath mates with the exterior surface of the implant when the implant is fitted within the polymer sheath.

11. A system as in claim 1, wherein the implant has an exterior surface that is ribbed.

12. A system as in claim 1, further comprising an abutment adapted to be fixed to the rigid implant, the abutment permitting attachment of a dental prosthesis.

13. The system as in claim 12, wherein the abutment is incorporated integrally into the implant.

14. A system as in claim 12, wherein the polymer sheath, the implant, and the abutment, when coupled together and inserted within a jawbone, form a support structure that permits attachment of a dental prosthesis.

15. A system as in claim 14, wherein the prosthesis is a single crown.

16. A system as in claim 14, wherein the prosthesis is a bridge.

17. A system as in claim 15, wherein multiple support structures support a dental prosthesis.

18. A system as in claim 17, wherein the prosthesis is a bridge.

19. A system as in claim 1, wherein expansion of the sheath upon insertion of the implant results in immediate stability of the sheath within the jaw bone.

20. A system as in claim 12, wherein the support structure and prosthesis can be inserted in a single office visit.

21. A method of installing a dental prosthesis comprising the steps of:

providing a system as in claim 12;

preparing a site within a jawbone;

inserting the polymer sheath into the prepared site;

inserting the implant within the sheath, thereby causing expansion of the sheath within the jawbone;

coupling the abutment to the implant; whereby the sheath, the implant, and the abutment form a support structure for a dental prosthesis; and attaching a dental prosthesis to the abutment.

22. The method as in claim 21, wherein the abutment is integral with the implant.

23. The method of claim 21, wherein site preparation consists of drilling a hole in the jawbone for an interference fit of the implant system.

24. The method of claim 21, wherein site preparation consists of tapping a hole in the jawbone for a threaded fit of the implant system.

25. The method of claim 21, wherein inserting the polymer sheath into the site consists of threading the sheath into the hole.

26. The method of claim 21, wherein inserting the implant within the sheath consists of threading the implant within the sheath.

27. A method as in claim 21, wherein the prosthesis is a crown.

28. A method as in claim 21, wherein the prosthesis is a bridge.

29. A method as in claim 21 comprising the further step of:

implanting a plurality of support structures into the jawbone.

30. A method as in claim 29 further, comprising the step of attaching a bridge to the support structures.

31. A method of inserting a dental implant, comprising the steps of providing a system as in claim 1;

preparing a site within a jawbone;

inserting the polymer sheath into the prepared site; and inserting the implant within the sheath, thereby causing expansion of the sheath within the jawbone.

* * * * *